US008273687B2

(12) United States Patent
Messerschmidt et al.

(10) Patent No.: US 8,273,687 B2
(45) Date of Patent: *Sep. 25, 2012

(54) LIMONENE-CONTAINING HERBICIDE COMPOSITIONS, HERBICIDE CONCENTRATE FORMULATIONS AND METHODS FOR MAKING AND USING SAME

(75) Inventors: Olav Messerschmidt, East Lansing, MI (US); Joseph Jankauskas, Dacula, GA (US); Frank Smith, Yuba City, CA (US)

(73) Assignee: Cutting Edge Formulations, Inc., Buford, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/776,610

(22) Filed: May 10, 2010

(65) Prior Publication Data

US 2010/0216644 A1 Aug. 26, 2010

Related U.S. Application Data

(63) Continuation of application No. 11/733,572, filed on Apr. 10, 2007, now abandoned, which is a continuation of application No. 11/071,398, filed on Mar. 2, 2005, now abandoned.

(51) Int. Cl.
*A01N 27/00* (2006.01)
(52) U.S. Cl. .................................................... 504/357
(58) Field of Classification Search ........................ None
See application file for complete search history.

(56) References Cited

U.S. PATENT DOCUMENTS

| | | | |
|---|---|---|---|
| 2,512,044 A | 6/1950 | Swaney et al. | |
| 3,397,053 A | 8/1968 | Bordenca et al. | |
| 3,564,046 A | 2/1971 | Newhall | |
| 3,592,910 A | 7/1971 | Clark et al. | |
| 3,960,539 A | 6/1976 | Newhall | |
| 4,587,123 A | 5/1986 | Price | |
| 5,139,562 A | 8/1992 | Vaughn et al. | |
| 5,336,428 A * | 8/1994 | Kaplan et al. | 510/188 |
| 5,403,587 A | 4/1995 | McCue et al. | |
| 5,407,899 A | 4/1995 | Howell | |
| 5,741,502 A | 4/1998 | Roberts | |
| 5,753,593 A * | 5/1998 | Pullen et al. | 504/150 |
| 5,834,533 A | 11/1998 | Patel et al. | |
| 5,925,182 A | 7/1999 | Patel et al. | |
| 5,951,992 A | 9/1999 | Wilkins | |
| 5,998,335 A | 12/1999 | Selga et al. | |
| 6,010,978 A | 1/2000 | Lauilhe et al. | |
| 6,277,389 B1 | 8/2001 | Pullen | |
| 6,500,445 B1 | 12/2002 | Pullen | |
| 6,582,712 B2 | 6/2003 | Pullen | |
| 6,613,728 B1 | 9/2003 | Sirianni et al. | |
| 6,759,370 B1 | 7/2004 | Innes | |
| 2004/0092606 A1 | 5/2004 | McPartland | |
| 2004/0248764 A1 | 12/2004 | Franklin | |

FOREIGN PATENT DOCUMENTS

| | | | |
|---|---|---|---|
| DE | 504333 | | 7/1930 |
| WO | WO 93/19598 | | 10/1993 |
| WO | WO 94/22304 | | 10/1994 |
| WO | WO 97/16975 | | 5/1997 |
| WO | WO-9716975 | * | 5/1997 |
| WO | WO 00/49865 | | 8/2000 |
| WO | WO-0049865 | * | 8/2000 |
| WO | WO 2004/021787 A | | 3/2004 |

OTHER PUBLICATIONS

Vaughn et al., Votatile Monoterpenes as Potential Parent Structures for New Herbicides, Weed Science, vol. 41, pp. 114-119, 1993.*
Agricultural & Food Chem., vol. 7, No. 4, 1959, pp. 264-268, Krewson, Wood, & Wolfe, Eastern Reg Research Lab, "Plant Growth Regulators: Synthesis & Biological Activity of Some Quaternary Ammonium and Related Compounds That Suppress Plant Growth".
American Chemical Society, 1988, Chapter 16, pp. 250-261, Stella D. Elakovich, Department of Chemistry, University of Southern Mississippi, "Terpenoids as Models for New Agrochemicals".
American Potato Journal, 1991, vol. 68, pp. 821-831, Steven F. Vaughn and Gayland F. Spencer, "Volatile Monoterpenes Inhibit Potato Tuber Sprouting".
Ann. Appl. Biol, 2002, 141:111-116 (printed in Great Britain), H P Singh, Daizy R. Batish, S Kaur, H Ramezani and R K Kohli, Department of Botany, Panjab University, India, "Comparative phytotoxicity of four monoterpenes against *Cassia occidentalis*".
Biologically active natural products: Potential use in agriculture. American Chemical Society symposium series (1988) H.G. Cutler Editor, Washington D.C., Chapter 16 "Terpenoids as models for New Agrochemicals" by S.D. Elakovich pp. 250-261.
British Crop Protection Conference, 1985, pp. 265-270, J.W. May, J.R. Goss, Shell Development Company, J.M. Moncorge, Agrishell, M.W. Murph, Shell Research Limited, "A Versatile New Herbicide with Wide Spectrum Crop Use".

(Continued)

*Primary Examiner* — Alton Pryor
(74) *Attorney, Agent, or Firm* — Woodard, Emhardt, Moriarty, McNett & Henry LLP

(57) ABSTRACT

Provided are methods, kits and compositions for killing, controlling or suppressing a plant by administering to surfaces of the plant a herbicide composition comprising a herbicidally effective limonene component and an emulsifying agent in an aqueous emulsion, wherein the composition has a pH greater than 5. Also provided are methods, kits and compositions for killing, controlling or suppressing a plant, comprising administering to surfaces of the plant a herbicide composition comprising a herbicidally effective limonene component and an emulsifying agent in an aqueous emulsion, wherein the composition includes a wetting agent. Also provided are methods, kits and compositions for killing, controlling or suppressing a plant, comprising administering to surfaces of the plant a herbicide composition comprising a herbicidally effective limonene component and an emulsifying agent in an aqueous emulsion, wherein the composition has a pH greater than 5 and includes a wetting agent.

16 Claims, 8 Drawing Sheets

OTHER PUBLICATIONS

Bulletin of Torrey Botanical Club, 1964, 91(4) pp. 327-330, W.H. Muller and C.H. Muller, "Volatile Growth inhibitors produced by Salvia species".
Derwent Abstract Accession No. 87-286557, (Shell Int. Res. Miy BV) Oct. 14, 1987.
Derwent Abstract Accession No. 88-119336, WO-A-8802598 (Du Pont De Nemours Co) Apr. 21, 1988.
Derwent Abstract Accession No. 88-216573, JP A 63-152303, (Mitsubishi Petroch KK) Jun. 24, 1988.
Derwent Abstract Accession No. 88-231637 JP A 63-165301, (Shell Kagaku KK) Jul. 8, 1988.
Derwent Abstract Accession No. 90-284353, EP 388164, (Du Pont De Nemours Co.) Sep. 19, 1990.
Derwent Abstract Acession No. 91-152274, (Sanyo Chem Ind Ltd), Apr. 11, 1991.
D-Limonene Product Data Sheet, 2003, Florida Chemical Co., Inc., www.floridachemical.com.
Dow Surfactants, Surfactant Basics http://www.dow.com/surfactants/faq.
EPA R.E.D. Facts, 1994, EPA-738-F-94-030, "Overview of EPA 1994 Review of Limonene".
International Journal of Science, 1969, vol. 223, No. 5209, pp. 965-966, William F. Newhall, University of Florida, Correlation of Pseudocholinesterase Inhibition and Plant Growth Retardation by Quaternary Ammonium Derivatives of (+)-Limonene.
Journal of Chemical Ecology (1989), 15(5), pp. 1567-1577, G.B. Williamson et al., Chemical Inhibition of fire-prone grasses by fire-sensitive shrub, *Conradina canescens*.
Journal of Chemical Ecology 1985, 11(11), pp. 1527-1534, I.S. AlSaadawi et al., Alleopathic effects of *Citrus aurantium* L. II. Isolation, characterization, an Biological Activities of Phytotoxins.
Journal of Chemical Ecology, 1989, vol. 15, No. 5, pp. 1567-1577, G. Bruce Williamson, Nikolaus H. Fischer, Donald R. Richardson, and Ana De La Pena, Louisiana State University, "Chemical Inhibition of Fire-Prone Grasses by Fire-Sensitive Shrub, *Conradina canescens*".
Journal of Chemical Ecology, 2000, vol. 26, No. 3, pp. 611-624, Denise Abrahim, Wellington L. Braguini, Ana M. Kelmer-Bracht and Emy L. Ishii-Iwamoto, "Effects of Four Monoterpenes on Germination, Primary Root Growth, and Mitochondrial Respiration of Maize".
Journal of Essential Oil Research, 1993, Nov./Dec. Issue, pp. 651-657, Massimo Maffei, Silvano Scannerini and Marco Mucciarelli, University of Turin Viale, Paraquat on Carvone Biosynthesis in Mentha.
Journal of the Science of Food and Agriculture, 2004, vol. 84, Issue 11, pp. 1319-1326, MA Ibrahim, EJ Oksanen, JK Holopainen, Department of Ecology and Environmental Science, University of Kuopio, "Effects of limonene on the growth and physiology of cabbage and carrot plants".
Journal of the Weed Science Society of American, 1996, vol. 44, pp. 6-11, Robert L. Zimdahl, "Weed Science".
Kim H. Haag—Effects of Herbicide Application on Mortality and Dispersive Behavior of the Water Hyacinth Weevils, *Neochetina eichhorniae* and *Neochetina bruchi*, Environmental Entomology 15(6), 1192-1198 (1986).
Kirk-Othmer, Encyclopedia of chemical technology, Third Edition, vol. 22, pp. 709-712. John Wiley and Sons, New York.
MM-01 Herbicide Field Trial, 2004, "Modular Masonry".
Proc, Montana Acad. Sci., (1982), 41, pp. 51-56, T. Weaver and L. Kish, "Allelopathic potential of terpene secreting (aromatic) plants."
Proc. Br. Crop. Prot. Conf., 1985, vol. 1, pp. 265-270, J.W. May et al., "SD 95481 a versatile new Herbicide with wide spectrum crop use."
Quaternary Ammonium Compounds, 1966, William F. Newhall and A.P. Pieringer, University of Florida Citrus Experiment Station, "Derivatives of (+)-Limonene: Quaternary Ammonium Compunds That Retard Plant Growth".
Relationship of Surface Tension and Concentration http://chemistry.co.nz/surfactants.htm.
Special Report, Allelopathic Chemicals, 1983, Alan R. Putnam, Michigan State University, "Nature's herbicides in action".
The Amer. Midland Naturalist, 1970, vol. 83, pp. 254-282, R. del Moral and C.H. Muller The allelopathic effects of *Eucalyptus camaldulensis*.
The Merck Index, Tenth Edition, Merck and Co., Inc, Rahway N.J. U.S.A.Monographs 3840, 5321, 6658, 6668, 7319, 7320, 7321.
The Science of Allelopathy, John Wiley and Sons, New York, (1986), chapter 12, pp. (203)-218) N.H. Fischer, "The function of mono and sesquiterpenes as plant germination and growth regulators."
Vaughn et al. (Votatile Monoterpenes as Potential Parent Structures for New Herbicides, Weed Science, vol. 41, pp. 114-119, 1993).
Weed Control as Science, G.C. Klingman, John Wiley and Sons, Inc., USA, Sep. 1961 chapter 14 "Other Organic Herbicides" pp. 208-225, in particular pp. 208-218.

\* cited by examiner

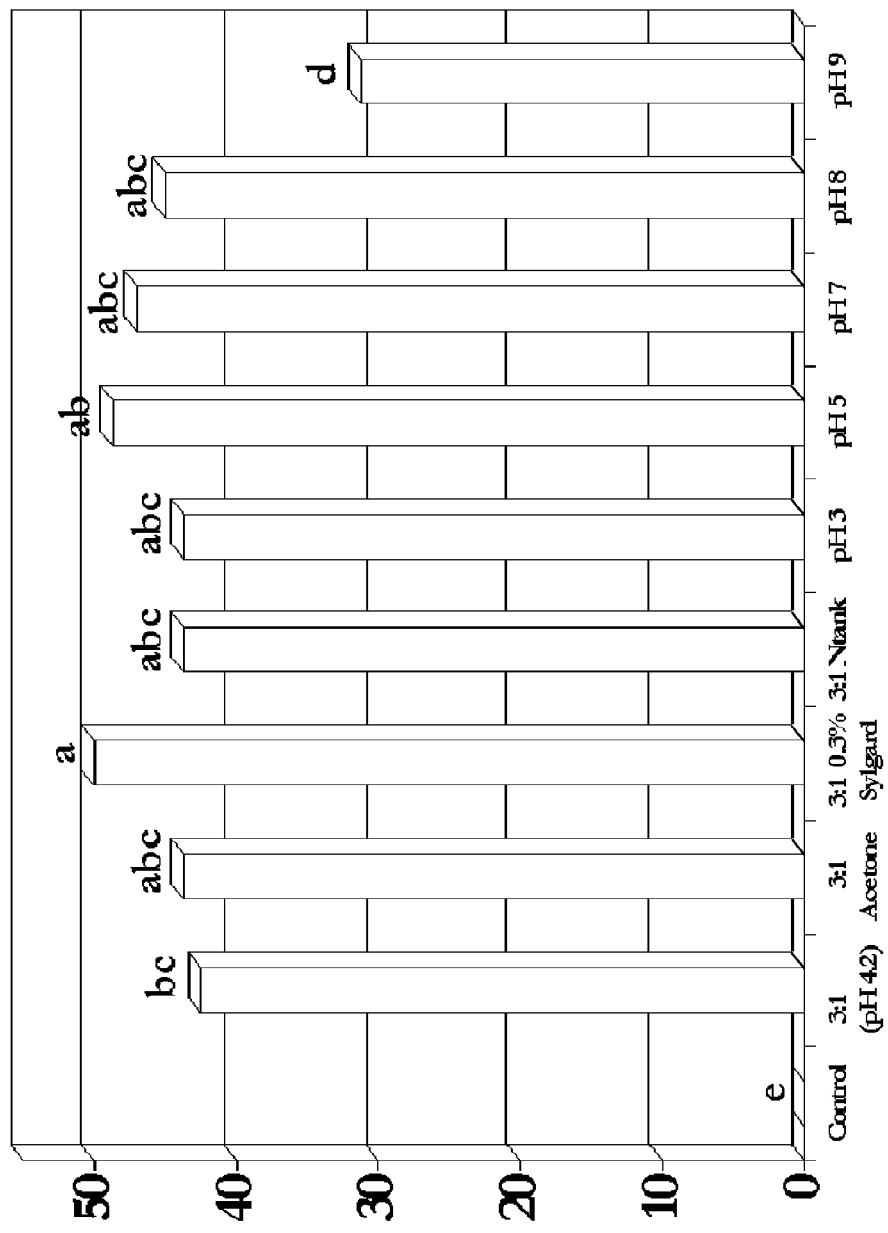

LIMONENE-CONTAINING HERBICIDE COMPOSITIONS, HERBICIDE CONCENTRATE FORMULATIONS AND METHODS FOR MAKING AND USING SAME

CROSS REFERENCE TO RELATED APPLICATIONS

This application is a continuation of U.S. patent application Ser. No. 11/733,572 filed on Apr. 10, 2007 now abandoned, which is a continuation of U.S. patent application Ser. No. 11/071,398 filed on Mar. 2, 2005, now abandoned, both of which are incorporated herein by reference in their entirety.

BACKGROUND

This invention relates to improvements in the field of herbicidal treatment of plants. The invention involves a method of herbicidal treatment of plants whereby unwanted plants and grasses are terminated using a formulation that is highly effective to non-selectively. kill plants it contacts. More particularly, the invention relates to "knock-down" herbicide formulations that comprise a herbicidally active limonene component.

By way of background, limonene is a naturally occurring chemical found in high concentrations in citrus fruits and spices. Limonene, otherwise known as orange limonene or 1-methyl-4-(1-methylethenyl)cyclohexene or 4-isopropenyl-1-methyl cyclohexene, occurs naturally in various ethereal oils, particularly oils of lemon, orange, lime, grapefruit, caraway, dill and bergamot. It has a chemical formula of $C10H16$, a molecular weight of 136.2, and contains 88.1% Carbon and 11.8% Hydrogen by weight. The d-form of limonene is a liquid having a boiling point of 175.5-176 degrees centigrade.

Some limonene is prepared by extraction from plants of the mint family, a large quantity is obtained from citrus oils, which are typically 80-90% limonene, and some is obtained from pine oil. For example, d-limonene can be obtained from steam extraction of citrus peels of orange, lemon, lime, grapefruit and bergamot. Some of the extractions can contain as high as 90% d-limonene; however, to produce technical grades of d-limonene of higher purity, i.e., greater than about 95%, distillation of the oils is required. d-Limonene can also be synthesized chemically. d-Limonene has a pleasant citrus scent and it can be suitably used in any living environment.

In addition to uses as flavor additives in a. wide variety of foods and beverages and uses in perfume materials, d-limonene has also been used in household and industrial cleaning products. It is readily available from commercial sources such as Florida Chemical Company, Inc., and is available in three different grades, named untreated/technical grade, food grade and lemon-lime grade. The food grade comprises about 97% d-limonene, the untreated/technical grade about 95%, and the lemon-lime grade about 70%, the balance in each case being other terpene hydrocarbons and oxygenated compounds.

Limonene has become a valuable industrial chemical. It finds use as a solvent and cleaning agent (in the manufacture of synthetic pine oil), as an expectorant, as a wetting and dispersing agent, as a monomer in the manufacture of various polymeric resins, as a flavorant in many food products and a precursor in the synthesis of the flavorant carvone, and as a polymerization inhibitor in storage of the tetrafluoroethylene monomer used in the manufacture of polytetrafluoroethylene (PTFE). It is also used in many soaps and perfumes for its lemon-like flavor and odor. In addition, limonene is a registered active ingredient in at least 15 pesticide products used as insecticides, insect repellents, and dog and cat repellents. For example, pesticide products containing limonene are used for flea and tick control on pets, as an insecticide spray, an outdoor dog and cat repellent, a fly repellent tablecloth, a mosquito larvicide, and an insect repellent for use on humans.

Limonene is of relatively low acute toxicity taken orally. The U.S. Food and Drug Administration considers limonene Generally Recognized as Safe (GRAS) as a food additive or flavoring, and as a fragrance additive. The U.S. Environmental Protection Agency has granted limonene an exemption from the requirement of a tolerance when it is used as an inert ingredient in pesticide formulations, and when used as an insect repellent tablecloth.

Turning now to consideration of herbicides, a wide range of chemicals are used to control weeds in the agricultural industry and to control unwanted vegetation in the landscaping industry. The aim of herbicides is to prevent weeds and unwanted plants from competing with a desired crop in the case of agricultural uses, or competing with preferred vegetation in landscaping applications.

At present, there-are two main classes of herbicidal chemicals that are used in connection with terrestrial plants, which is the subject of the present invention. In particular, the herbicides are generally separated into those that have a "contact" action upon plants, and those that have a "systemic" action upon plants. Some herbicides have both a contact and systemic action on plants. Other types of herbicides act in other ways, such as, for example as soil sterilants.

Herbicides may either be selective or non-selective. Selective herbicides, for example "Treflan" (trifluralin), may be utilized for the selective destruction of certain types of grass. Non-selective herbicides such as "Roundup" (glyphosate) may be used as a general herbicide for destroying or controlling many different types of plants and grasses.

A large number of herbicides and plant hormones have been developed over the years. In the early days inorganic compounds such as sodium chlorate and sodium arsenite and various borate compounds were used. There were also developed other organic herbicides such as Nphenylcarbamate, "Randox", and other chlorinated phenoxy compounds. In addition, industrial waste products were quite common. Later on, the hormone type weed killers 2,4-D (2,4-dichloro-phenoxyacetic acid) and 2,4,5-T (2,4,5-trichloro-phenoxyacetic acid) were developed, and have become quite common. More complicated organic weed killers and proprietary chemicals such as "Network" or "Roundup" (both glyphosates) have also been developed.

In many cases herbicides have deleterious effects. For example, they may poison beneficial crops, affect other plants or animals, and/or poison the soil. In addition, many herbicidal compositions presently on the market are highly toxic to humans and domestic animals. Most chemical herbicides are dangerous to mankind and are therefore dangerous when accidentally inhaled and/or absorbed into human and animal tissue. Because of the widespread concern of the deleterious side effects of currently available herbicides, and the problems associated with absorption and ingestion into other living matter, there is much concern as to the long-term use of complex and highly dangerous chemicals, especially when they enter into the food chain. A herbicide having lower toxicity is desirable.

There has been developed recently a relatively nontoxic herbicide which has fatty acids as its main constituents. This herbicide has a smothering effect on plants, however its efficacy is limited particularly in controlling perennial weeds. A further disadvantage is that the fatty acids are not readily carried or emulsified within an appropriate carrier fluid or solvent, which lessens its overall effectiveness due to the difficulties encountered in delivering the herbicide to plants.

It has been suggested recently that limonene can be used at a high concentration as a knock-down herbicide. In U.S. Pat. No. 5,998,335 to Selga et al., knock-down herbicidal compositions are described, one of which comprises about 95-96% by weight of d-limonene and about 4-5% of other components. The '335 patent reports that when this composition was applied to vegetation as a fine droplet spray (targeting 60-80% coverage of vegetation), most vegetation showed visible signs of stress (e.g., wilting or browning) within 2 to 24 hours of application of the herbicide. Selga et al. also reported in the '335 patent that an emulsified mixture of 60% d-limonene with water and commercial emulsifier was also tested. When this formulation was applied to vegetation as described above, most vegetation began showing visible signs of stress within 2 to 36 hours.

One disadvantage of the herbicides described by Selga et al. is that such high concentrations and volumes of limonene would be cost prohibitive and cumbersome for spraying large areas. These formulations also present practical challenges associated with effectively atomizing and spraying such oily or highly viscous compositions.

In light of the above, there is a continuing need for environmentally-friendly herbicides having increased efficiency and efficacy. The present invention addresses this need and provides a wide variety of benefits and advantages.

SUMMARY

In one form, the present invention provides a method for killing, controlling or suppressing a plant by spraying onto one or more leaves of the plant a liquid herbicidal composition including water, a herbicidally active limonene component, an emulsifying agent and a pH modifier effective to provide a pH greater than 5. As will be appreciated by a person of ordinary skill in the art, limonene is acidic and when dissolved in water will lower the pH typically to range of about 4 to 5.

In another form, the invention provides a method for making a herbicide composition, the method including: (1) providing a liquid herbicide formulation, the herbicide formulation including a herbicidally active limonene component and an emulsifying agent; (2) diluting the formulation with water to provide a herbicide composition; and (3) mixing into the herbicide composition a pH modifier effective to provide a pH greater than 5. In alternative embodiments, the pH modifier can be provided in the formulation with the herbicidally active limonene component and emulsifying agent, or can be dissolved or dispersed in the water prior to dilution of the formulation.

In yet another form of the invention, there is provided a kit for non-selective burn down of plants. The kit includes a container having therein a liquid herbicide, the herbicide including water, a herbicidally active limonene component, an emulsifying agent and a pH modifier effective to provide a pH greater than 5; and instructions, recorded in a medium, for applying the herbicide to a pre-selected area for indiscriminately killing, controlling or suppressing plants growing in the area.

In still another form of the invention, there is provided a kit for non-selective burn down of plants, the kit including a container having therein a liquid herbicide formulation, the herbicide formulation including a herbicidally active limonene component, an emulsifying agent and a pH modifier effective to provide a pH greater than 5; and instructions, recorded in a medium, for diluting the formulation to provide a herbicide composition. Also recorded in the medium in some embodiments are instructions for applying the herbicide composition to a pre-selected area for indiscriminately killing, controlling or suppressing plants growing in the area.

In another embodiment, the invention provides a kit for non-selective burn down of plants that includes a container having therein a liquid herbicide formulation, the herbicide formulation including a herbicidally active limonene component and an emulsifying agent; and instructions, recorded in a medium, for diluting the formulation with water and adding a pH modifier effective to provide a pH greater than 5. Also recorded in the medium in some embodiments are instructions for applying the herbicide composition to a pre-selected area for indiscriminately killing, controlling or suppressing plants growing in the area.

In another form, the invention provides a "knockdown" herbicidal composition effective against mature weeds including water, a herbicidally active limonene component, an emulsifying agent and a pH modifier effective to provide a pH greater than 5.

In another aspect of the invention, there is provided a method for killing, controlling or suppressing a plant, which includes providing a liquid herbicidal composition including water, a herbicidally active limonene component, an emulsifying agent and a wetting agent; and spraying the herbicidal composition onto one or more leaves of the plant.

The invention also provides a method for making a herbicide composition that includes: (1) providing a liquid herbicide formulation, the herbicide formulation including a herbicidally active limonene component and an emulsifying agent; (2) diluting the formulation with water to provide a herbicide composition; and (3) mixing into the herbicide composition a wetting agent.

In another form of the invention, there is provided a kit for non-selective burn down of plants that includes a container having therein a liquid herbicide, the herbicide including water, a herbicidally active limonene component, an emulsifying agent and a wetting agent; and instructions, recorded in a medium, for applying the herbicide to a pre-selected area for indiscriminately killing, controlling or suppressing plants growing in the area.

In another embodiment of the invention, there is provided a kit for non-selective burn down of plants that includes a container having therein a liquid herbicide formulation, the herbicide formulation including a herbicidally active limonene component and an emulsifying agent; and instructions, recorded in a medium, for diluting the formulation and mixing in a wetting agent to provide a herbicide composition. Also recorded in the medium in some embodiments are instructions for applying the herbicide composition to a pre-selected area for indiscriminately killing, controlling or suppressing plants growing in the area.

A "knock-down" herbicidal composition effective against mature weeds is also provided, the composition including water, a herbicidally active limonene component, an emulsifying agent and a wetting agent.

In another aspect of the invention, there is provided a method for killing, controlling or suppressing a plant, including: (1) providing a liquid herbicidal composition including water, a herbicidally active limonene component, an emulsifying agent, a wetting agent and a pH modifier effective to provide a pH greater than 5; and (2) spraying the herbicidal composition onto one or more leaves of the plant.

In another form of the invention, there is provided a method for making a herbicide composition that includes: (1) providing a liquid herbicide formulation, the herbicide formulation including a herbicidally active limonene component and an emulsifying agent; (2) diluting the formulation with water to provide a herbicide composition; and (3) mixing into the herbicide composition a wetting agent and a pH modifier effective to provide a pH greater than 5.

The invention also provides a method for making a herbicide composition, the method including: (1) providing a liquid herbicide formulation, the herbicide formulation including a herbicidally active limonene component, an emulsifying agent and a pH modifier effective to provide a pH greater than 5; (2) diluting the formulation with water to provide a herbicide composition; and (3) mixing into the herbicide composition a wetting agent.

In another aspect of the invention, there is provided a kit for non-selective burn down of plants that includes a container having therein a liquid herbicide, the herbicide including water, a herbicidally active limonene component, an emulsifying agent, a wetting agent and a pH modifier effective to provide a pH greater than 5; and instructions, recorded in a medium, for applying the herbicide to a preselected area for indiscriminately killing, controlling or suppressing plants growing in the area.

Another kit for non-selective burn down of plants provided by the invention includes a container having therein a liquid herbicide formulation, the herbicide formulation including a herbicidally active limonene component, an emulsifying agent and a pH modifier effective to provide a pH greater than 5; and instructions, recorded in a medium, for diluting the formulation and adding a wetting agent to provide a herbicide composition. Also recorded in the medium in some embodiments are instructions for applying the herbicide composition to a pre-selected area for indiscriminately killing, controlling or suppressing plants growing in the area.

Still another kit for non-selective burn down of plants provided by the invention includes a container having therein a liquid herbicide formulation, the herbicide formulation including a herbicidally active limonene component and an emulsifying agent; and instructions, recorded in a medium, for diluting the formulation with water and adding a wetting agent and a pH modifier effective to provide a pH greater than 5. Also recorded in the medium in some embodiments are instructions for applying the herbicide composition to a pre-selected area for indiscriminately killing, controlling or suppressing plants growing in the area.

In yet another form of the invention, there is provided a "knock-down" herbicidal composition effective against mature weeds including water, a herbicidally active limonene component, an emulsifying agent, a wetting agent and a pH modifier effective to provide a pH greater than 5.

Further objects, features, aspects, forms, advantages and benefits shall become apparent from the description and drawings contained herein.

While the actual nature of the invention covered herein tan only be determined with reference to the claims appended hereto, certain forms and features, which are characteristic of the preferred embodiments disclosed herein, are described briefly as follows.

BRIEF DESCRIPTION OF THE FIGURES

FIG. 8 is a bar graph setting forth results from a greenhouse study on lambsquarters conducted in Michigan in January of 2005. Ratings are based on 0 to 100% (no damage to dead). Statistical analysis is by Duncan's MRT ($P\_<0.05$) Treatments with the same letter or letter combination are not significantly different.

DETAILED DESCRIPTION OF THE PREFERRED EMBODIMENTS

Figure 1:
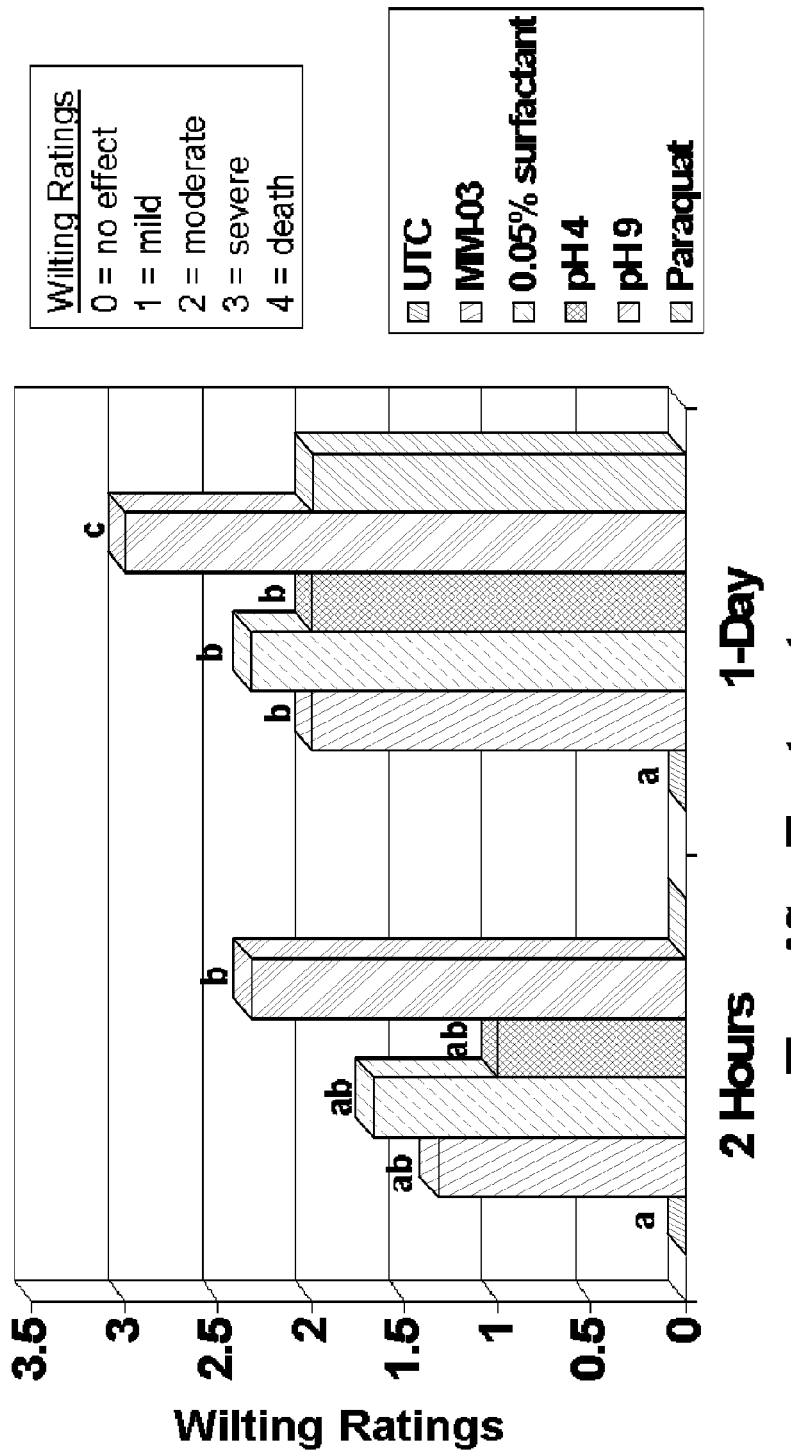
FIG. 1 is a bar graph setting forth the wilting assessment results at 2 and 24 hours from a field study of common grasses and broadleaves in turf conducted in November of 2004. Statistical analysis is by Duncan's MRT ($P \ll 0.05$). Treatments with the same letter or letter combination are not significantly different.
Figure 2:
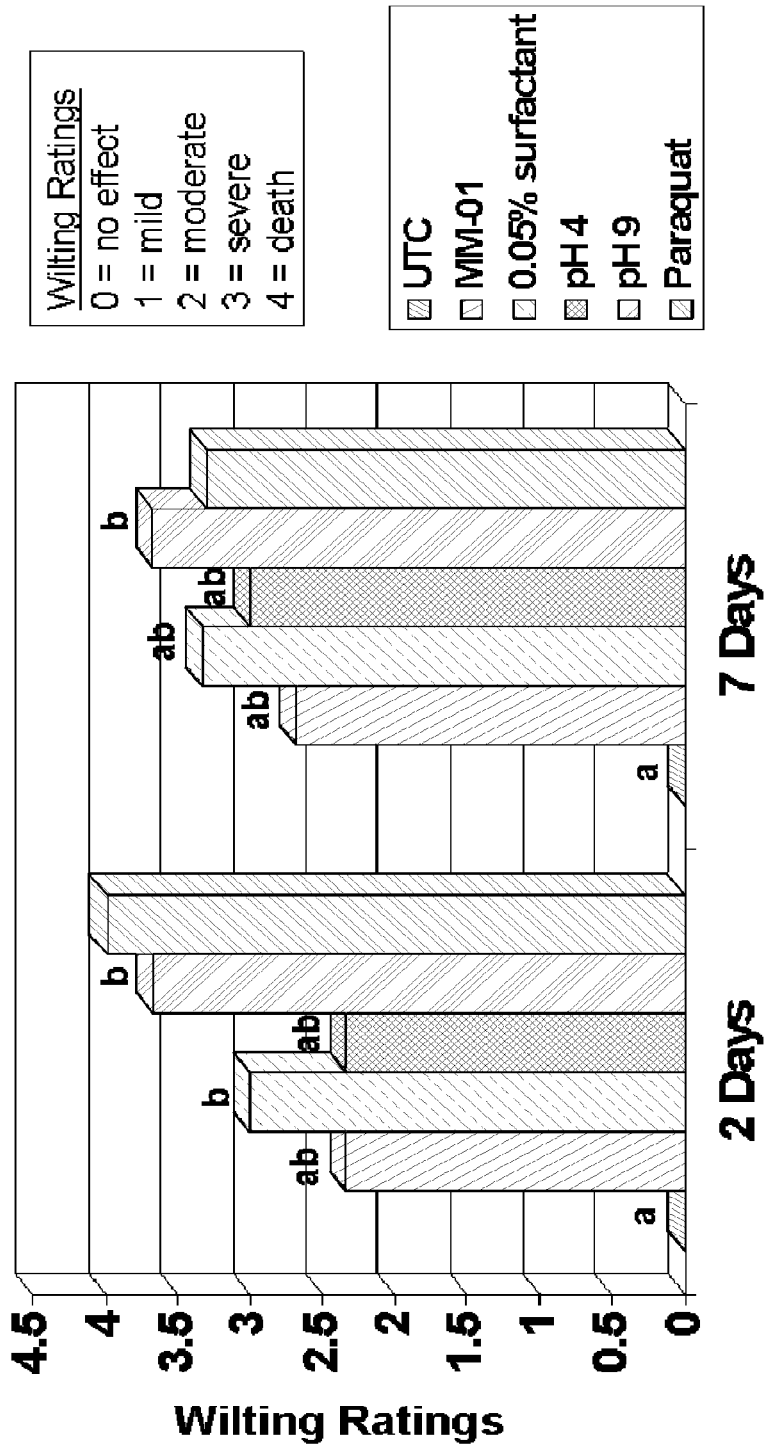
FIG. 2 is a bar graph setting forth the wilting assessment results at 2 and 7 days from a field study of common grasses and broadleaves in turf conducted in November of 2004. Statistical analysis is by Duncan's MRT ($P<0.05$). Treatments with the same letter or letter combination are not significantly different.
Figure 3:
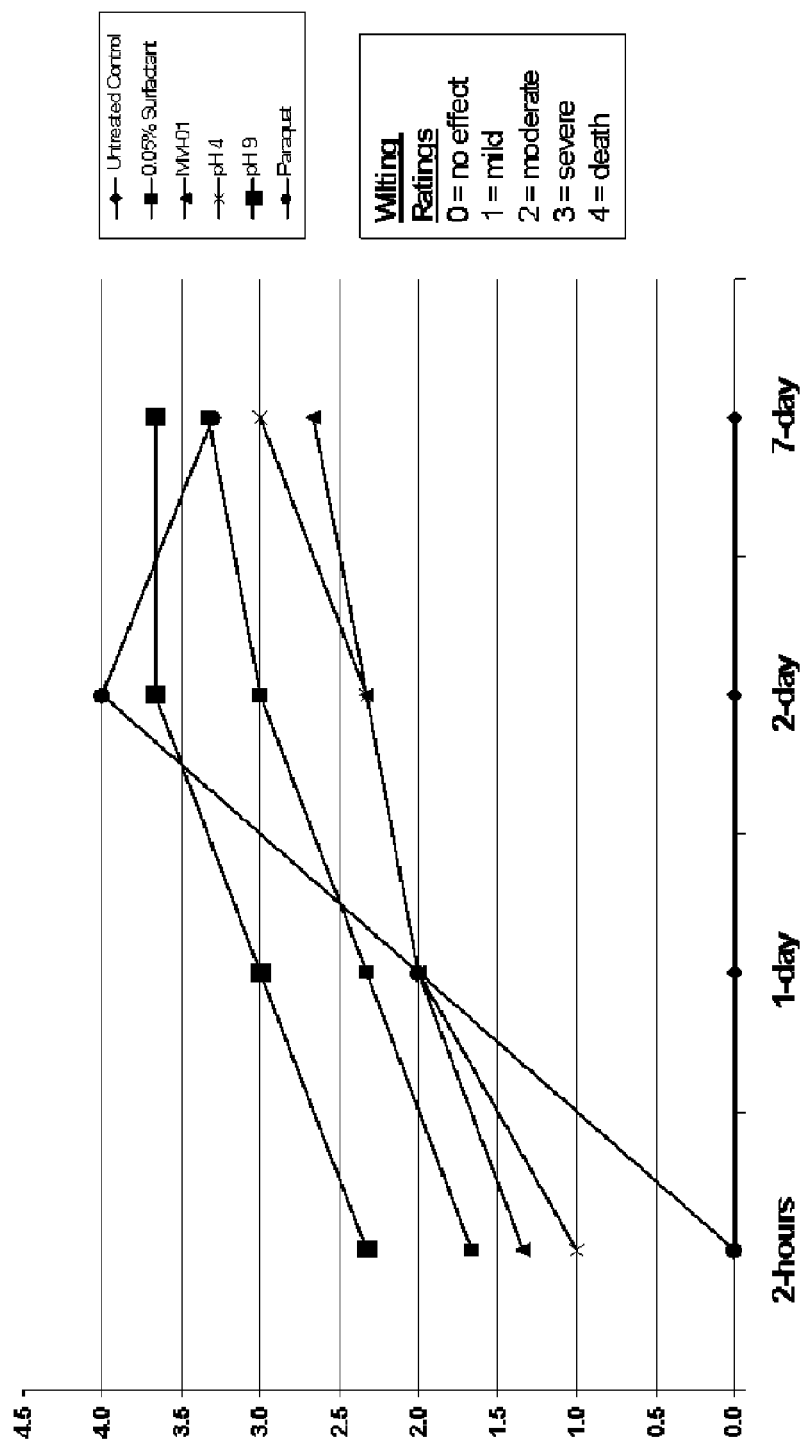
FIG. 3 sets forth a plot of the data presented in FIGS. 1 and 2.
Figure 4:
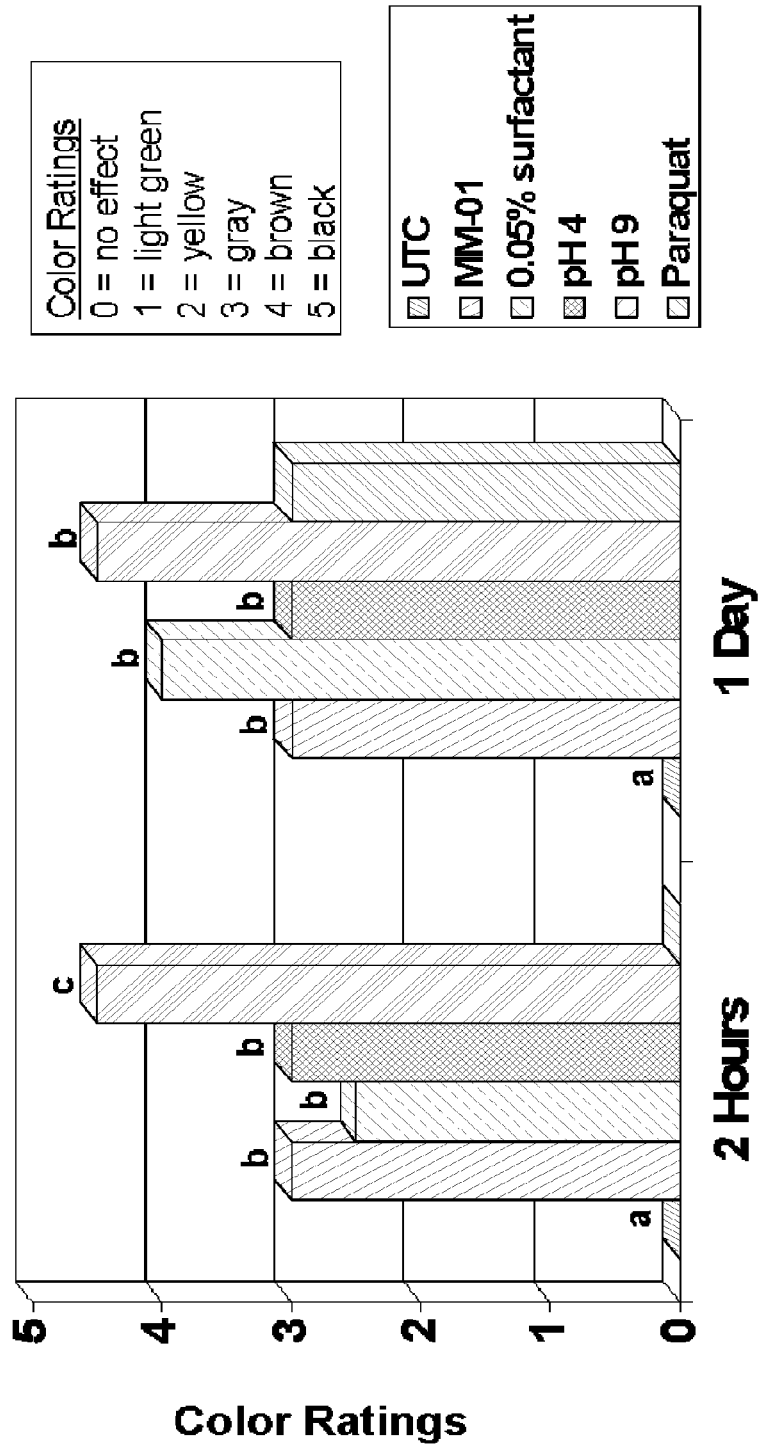
FIG. 4 is a bar graph setting forth the color assessment results at 2 and 24 hours from a field study of common grasses and broadleaves in turf conducted in November of 2004. Statistical analysis is by Duncan's MRT ($P\_<0.05$) Treatments with the same letter or letter combination are not significantly different.
Figure 5:
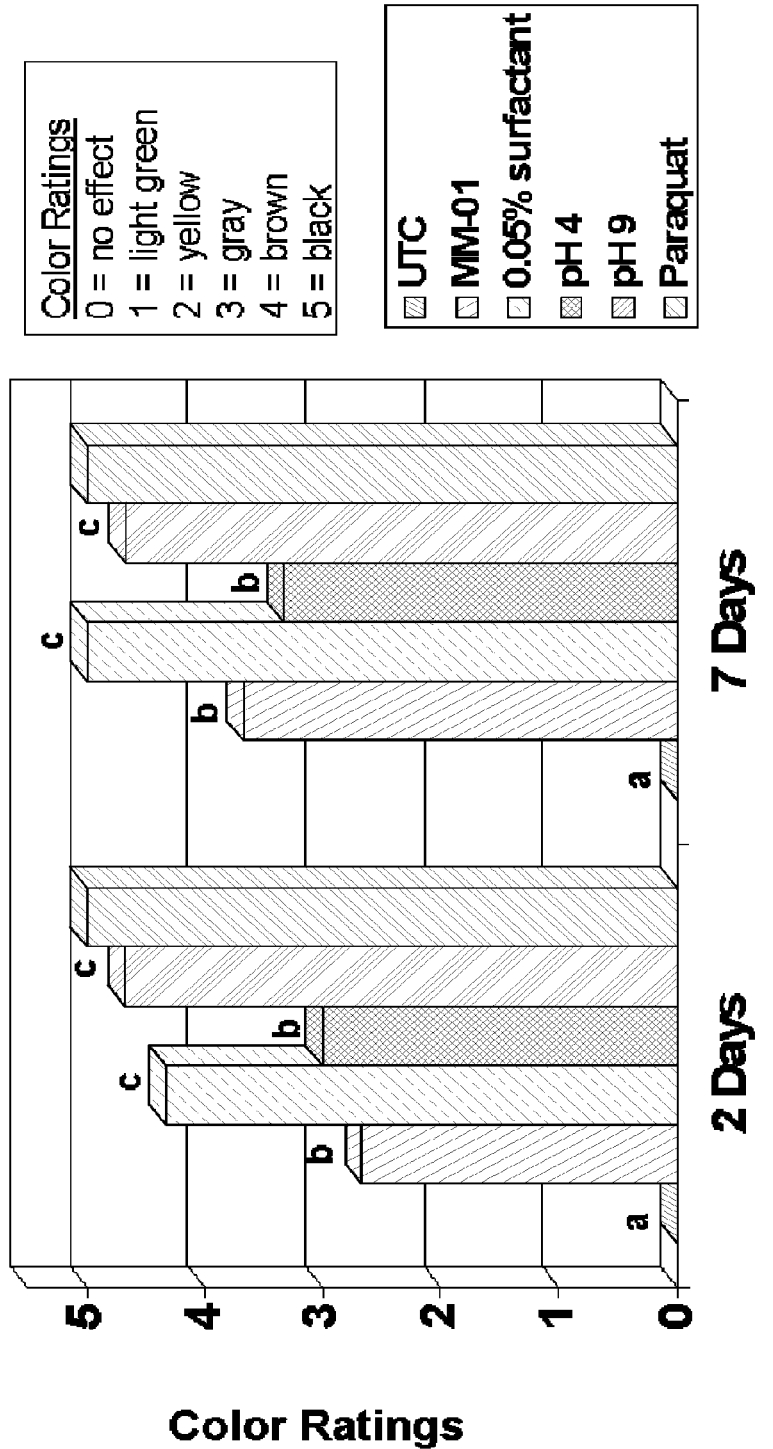
FIG. 5 is a bar graph setting forth the color assessment results at 2 and 7 days from a field study of common grasses and broadleaves in turf conducted in November of 2004. Statistical analysis is by Duncan's MRT (P-0.05). Treatments with the same letter or letter combination are not significantly different.
Figure 6:
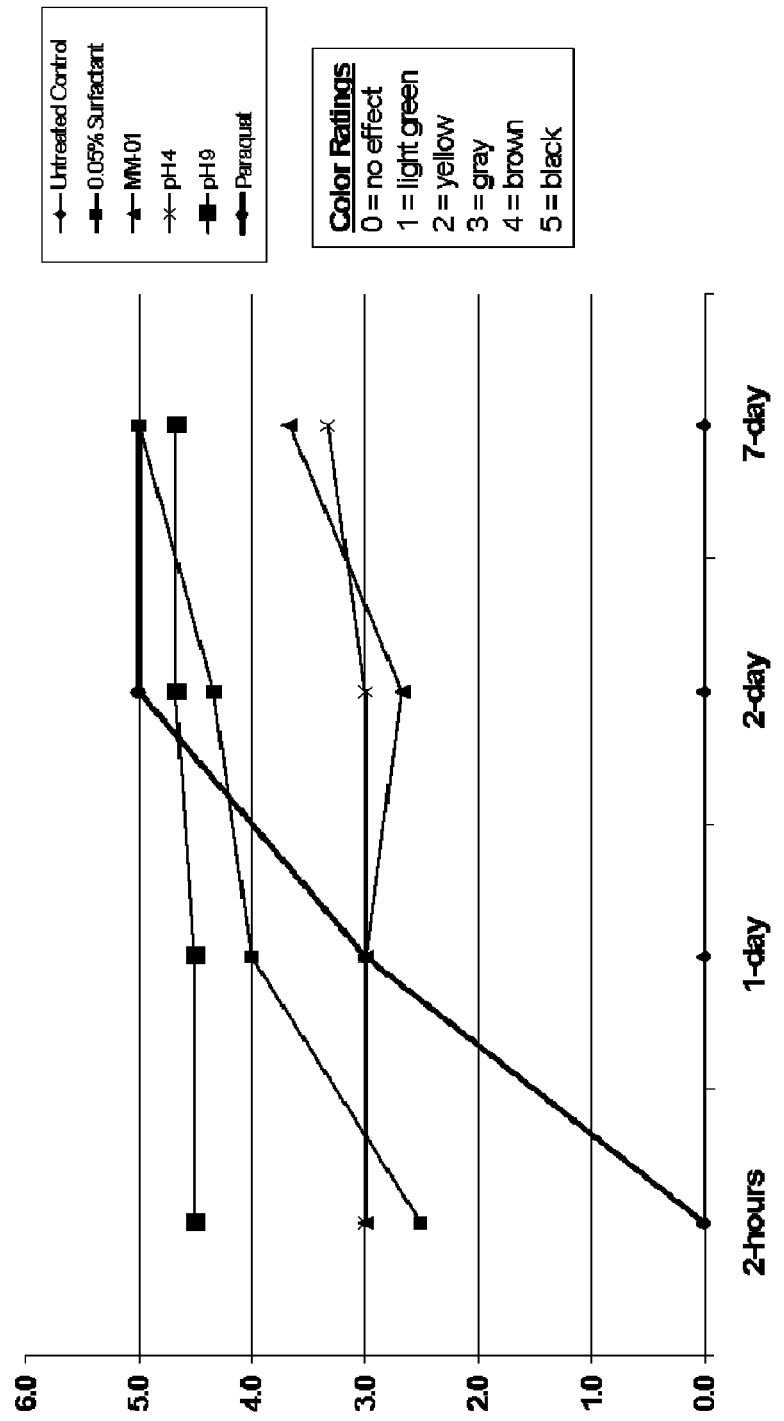
FIG. 6 sets forth a plot of the data presented in FIGS. 4 and 5.

For the purposes of promoting an understanding of the principles of the invention, reference will now be made to the embodiments described herein and specific language will be used to describe the same. It will nevertheless be understood that no limitation of the scope of the invention is thereby intended. Any alterations and further modifications in the described fluids, methods, devices or kits, and any further applications of the principles of the invention as described herein, are contemplated as would normally occur to one skilled in the art to which the invention relates.

It has been discovered that the effectiveness of limonene compositions as non-selective, "burn down" herbicides can be significantly improved by increasing the pH of the composition to a pH of greater than 5, by including a wetting agent in the composition, or both. Accordingly, this invention provides in one embodiment a method of killing, controlling or suppressing a plant by administering to surfaces of the plant a herbicide composition comprising a herbicidally effective limonene component and an emulsifying agent in an aqueous emulsion, wherein the composition has a pH greater than 5. In another embodiment, the invention provides a method of killing, controlling or suppressing a plant by administering to surfaces of the plant a herbicide composition comprising a herbicidally effective limonene component and an emulsifying agent in an aqueous emulsion, wherein the composition includes a wetting agent. In yet another embodiment of the invention, there is provided a method of killing, controlling or suppressing a plant by administering to surfaces of the plant a herbicide composition comprising a herbicidally effective limonene component and an emulsifying agent in an aqueous emulsion, wherein the composition has a pH greater than 5 and includes a wetting agent.

In this description of the invention, the term "herbicidal" or "herbicidally effective" refers to the quality of being effective to kill, control or suppress a plant when at least a minimum amount of the herbicide composition contacts the plant. The term "kill" as used herein in relation to a herbicide means to cause the above-ground portion of a plant to irreversibly cease normal function, typically resulting in wilting and browning and/or necrosis of the normally green tissues of the plant. It is, of course, possible that a plant, particularly a perennial plant, that is killed within this meaning may "re-sprout" and produce new growth. The term "control" as used herein in relation to a herbicide means that, in a treated area, the plants experience at least about 90% mortality. The term mortality" as used herein can refer to a percentage of individual plants in the treatment area that are killed, or a percentage of the total mass or total surface area of vegetation in the treatment area that experiences wilting, bleaching, browning or necrosis. The term "suppress" is used herein in relation to a herbicide to mean that, in a treatment area, the plants experience from about 40 to about 90% mortality. Application of an inventive herbicide composition to the plant causes the plant, where contacted, to wilt, bleach, or brown, which results in necrosis of the leaf ("burn down" and oftentimes death of the plant.

Herbicide compositions in accordance with many preferred embodiments of the present invention are nonselective and non-systemic, and are effective against almost any vegetation, specifically against common crop and garden weeds, both annual and perennial. They are "contact herbicides" in that their action results from contact with plant surfaces rather than uptake by the plant. In addition, inventive formulations are "knockdown" (i.e. fast acting, typically within several hours) or "burn down" herbicides, which must be sprayed over a substantial portion of the above-ground part of the plant in order to have an optimal or desired effect. Conveniently, the herbicides are applied as a fine droplet spray. In addition, it is believed that inventive herbicides have optimal burn down effect in relatively warm temperatures and relatively dry conditions (relative to average temperatures and moisture for a given location). The active ingredient of the present herbicidal compositions has the advantage of being an environmentally friendly, natural product, which is unlikely to cause environmental pollution or create toxicity problems for humans or domestic animals.

While not to be bound by theory, it is believed that when a thin film of the herbicide composition covers all or a portion of the leaves and other green tissues of a target plant, the herbicidally active limonene component, under conditions present in the composition, may break down or dissolve the waxy layers of the plant, thereby causing the plant to lose the ability to prevent the loss of moisture to the environment. Since limonene-containing oils are natural oils, the non-toxic aqueous herbicide compositions of the invention are environmentally acceptable and have little, if any deleterious effect on humans, wildlife and non-target vegetation.

For purposes of clarity, the term "herbicide composition" is used herein to refer to a liquid that is actually contacted with a plant, such as from a sprayer, to achieve burn down in accordance with the invention. A herbicide composition of the invention can be made and provided to an end user as a pre-made (or "pre-mixed" or "ready to spray") herbicide composition in some forms of the invention. In other forms of the invention, the herbicide composition can be mixed by the end user at or near the place where the herbicide composition will be used by diluting a herbicide concentrate formulation and optionally adding other ingredients. As used herein, the terms "herbicide formulation" and "herbicide concentrate" and "herbicide concentrate formulation" are used interchangeably to refer to a formulation of ingredients in accordance with the invention that can be diluted with water, with the optional addition of other ingredients, to provide a herbicide composition. This manner of providing a herbicide concentrate formulation may be desirable, for example, where vegetation covering a large area is to be sprayed, for example, using commercial spraying equipment, and thus a great volume of the herbicide composition is needed. In such a case, a herbicide formulation can be provided to an end user, optionally together in a kit, with instructions for mixing the formulation with water, and perhaps other ingredients in or near the sprayer to provide a herbicide composition. Such herbicide formulations and herbicide kits are described further herein, but attention is first given to herbicide compositions of the invention.

In accordance with the invention, a non-selective, burn down herbicide composition includes a herbicidally active limonene component, an emulsifying agent and a hydrophilic solvent, preferably water, and that includes a wetting agent, or has a pH greater than 5, or includes a wetting agent and has a pH greater than 5.

The herbicidally active limonene component includes limonene or a limonene derivative in sufficient amount that it is effective, when in a herbicide composition provided in accordance with the present invention, to kill, control or suppress plants that are contacted with a sufficient amount of the herbicide composition. A sufficient amount is considered to be an amount contacting a sufficient surface of the plants to achieve a desired result. The herbicidally active limonene component can be a pure or substantially pure limonene or limonene extract, or a multi-component composition that includes limonene. In this regard, the herbicidally active limonene component can comprise an essential oil that includes limonene, preferably at least about 8% limonene by weight. For example, the limonene can be provided in the form of a citrus oil, a pine oil, eucalyptus oil or a tea tree oil, any of which can be the herbicidally active limonene component in accordance with the invention.

Furthermore, the herbicidally active limonene component can comprise a modified limonene, as long as the modified limonene has herbicidal activity in accordance with the invention. For example, based upon work that has been reported by others, it appears that oxygenation of limonene to provide limonene oxide may improve water solubility characteristics while maintaining similar burn-down functionality compared to unmodified limonene. Such modified limonene compounds are contemplated by the present invention, and are expressly included within the meaning of the term "herbicidally active limonene component."

In one preferred embodiment, the herbicidally active limonene component comprises a citrus oil, e.g. orange oil. In another preferred embodiment, the herbicidally active limonene component comprises d-limonene derived from a citrus oil. The fraction of the citrus oil comprising d-limonene can be separated off by vacuum distillation, or any other conventional separation process. d-Limonene is volatile, and is separated off in the distillate. The distillate is a highly concentrated composition of the d-limonene, comprising about 95-96% by weight of d-limonene and about 4-5% by weight of other components. This distillate may be utilized in a herbicidal composition of the present invention.

Although it is possible to use unrefined citrus oil, instead of the vacuum distillate, as discussed above, vacuum distillation (or other separation process, such as steam distillation (azeotroping), solvent extraction, supercritical extraction etc.) has the advantage of separating the herbicidally active ingredient from flavor components of the citrus oil. The flavor components then form a valuable by-product, which can be utilized in, for example, foodstuffs or pharmaceutical compositions.

Other terpenes, particularly monoterpenes, that have similar herbicidal properties to limonene in formulations as provided herein are considered equivalent to limonene for purposes of the present invention. Similarly, other natural oils having high terpene content and having similar herbicidal properties to the limonene-containing oils discussed above in formulations as provided herein are considered equivalent to the limonene-containing oils for purposes of the present invention. "High terpene content" as used herein means those natural oils having a terpene content of at least 50 percent. It is preferable that the natural oil contains at least 90 percent terpene. Such terpenes and terpene containing natural oils are expressly encompassed within the meaning of the term "herbicidally active limonene component" as used herein.

When pure or substantially pure limonene is used in an inventive herbicide composition, the herbicide composition preferably includes from about 8 percent to about 100 percent by weight of the limonene, preferably from about 12 percent to about 30 percent by weight and more preferably from about 15 percent to about 25 percent by weight. It is understood by a person of ordinary skill in the art that a herbicide composition having a lower concentration of limonene can be used to achieve a similar response by spraying a higher volume of the herbicide composition on the plant (increasing the volume increases the amount of limonene to which the plant is exposed).

When a terpene containing natural oil is used, the amount of the natural oil in the herbicide will depend upon the amount of terpenes in the specific oil used. In one embodiment, the herbicide composition includes from about 8 percent to about 100 percent by weight of such a natural oil, preferably from about 12 percent to about 30 percent by weight and more preferably from about 15 percent to about 25 percent by weight.

As discussed above, the remainder of the herbicide composition comprises water (or optionally another hydrophilic solvent), one or more emulsifying agents, and one or more of a wetting agent and a pH modifier.

The emulsifying agent is preferably a non-toxic emulsifying agent, and can be a surfactant or other emulsifying agent known in the art, or a mixture of one or more thereof. The emulsifying agents employed should be capable, when mixed with water and the herbicidally active limonene component, of forming an emulsion, preferably a homogeneous emulsion.

Useful emulsifying agents include lauryl dimethyl amine oxide, polyoxypropylene, polyoxyethylene block copolymers alcohol ethoxylate and nonylphenol ethoxylate. Alternatively, the emulsifying agent can be a polyethoxylated castor oil. One such emulsifying agent is available commercially under the trade name of Alkamuls EL620 from Rhone Poulenc Co. It is non-toxic to humans and animals and will not cause skin or eye irritation. Other commercially available emulsifying agents that are non-toxic, such as polyoxyethylenesorbitans supplied by ICI Americas or Sigma Chemical Company, may also be suitably used for the present invention. In a preferred embodiment a polyoxyethylenesorbitan monooleate such as Tween 80 may be used.

Surfactants such as anionic and nonionic surfactants are acceptable emulsifying agents for use in a herbicide composition of the present invention. Preferred anionic surfactants include salts of fatty acids, alkyl sulphates, alkyl ether sulphonates and alkyl aryl sulphonates. Preferred nonionic surfactants include silicone based and nonylphenol ethoxylate surfactants. Examples of preferred surfactants include about 10 percent sulfonic acid, about 6 percent to about 7 percent sodium laurel sulfate, from about 8 percent to about 12 percent alcohol ethoxylate and from about 1 percent to about 2 percent olefin sulfonate.

In general, the emulsifying agent should be present in an amount sufficient to render the herbicidally active limonene component miscible in the water or other hydrophilic solvent. Generally, the herbicide composition will contain from about 0.05 percent to about 10 percent by weight of one or more emulsifying agent, preferably from about 0.1 percent to about 0.5 percent by weight and more preferably from about 0.2 percent to about 0.4 percent by weight.

While an inventive herbicide composition will typically comprise an emulsion of a herbicidally active limonene component with water, an inventive composition can include another non-toxic hydrophilic solvent instead of or in addition to water, such as, for example, ethanol, dilute acetic acid solutions, and the like.

As stated above, in one embodiment of the invention, the herbicide composition has a pH greater than 5. In another embodiment, the herbicide composition has a pH of from about 5 to about 10. The pH of the naturally acidic limonene can be raised by including a pH modifier in the herbicide composition. Examples of pH modifiers that can be selected for use in connection with the invention include, without limitation, potassium carbonate, sodium hydroxide and potassium hydroxide. In one preferred embodiment, the pH of the composition can range from about 6 to about 8. In another preferred embodiment, the pH range of the herbicidal composition is from about 8 to about 10.

Thus, in certain preferred embodiments of the inventive, herbicide compositions, which are suitable for application as a spray, include about 8% to about 100% w/w %, preferably about 12% to about 30% w/w %, and more preferably from about 15% to about 25% by weight of a herbicidally active limonene component; from about 0.05% to about 10% w/w %, preferably about 0.1% to about 0.5% w/w %, and more preferably from about 0.2% to about 0.4% by weight of an emulsifying agent; a pH modifier in an amount effective to maintain a desired pH in the composition; and the balance of water or other selected hydrophilic solvent. In one preferred embodiment, there is provided a herbicide composition comprising a herbicidally active limonene component at a concentration of at least about 8% w/w %, an emulsifying agent effective to dissolve or disperse the herbicidally active limonene component in water, in an effective amount, a pH modifier effective to maintain a pH greater than 5, and a hydrophilic solvent, preferably water.

In another embodiment of the invention, the herbicide composition includes a wetting agent effective to improve the wetting properties, and possibly also the penetration properties, of the herbicide composition. When a wetting agent is included in a herbicide composition of the invention, the composition sprayed on the weeds or other vegetation can be applied at a lower rate (i.e., measured in gallons per acre) to achieve an equivalent result because the wetting agent causes each droplet of the composition to spread over a greater surface area of the plant. When a wetting agent is absent, the composition sprayed on a plant must cover a significantly greater surface area of the plant to achieve a similar result.

Many wetting agents suitable for use in herbicides are known to a person of ordinary skill in the art, and are available commercially. Examples of wetting agents that can be selected for use in connection with the invention include, without limitation, nonylphenol ethoxylate, and anionic, cationic and nonionic (including silicone based) surfactants and methylated seed oil. Particularly preferred wetting agents are silicone surfactants. In one preferred embodiment, the composition includes from about 0.02% to about 1.0% w/w % of a wetting agent. In another preferred embodiment, the herbicide composition includes from about 0.05% to about 0.5% w/w %, more preferably from about 0.1% to about 0.2% w/w %, of a wetting agent.

Thus, in certain preferred embodiments of the inventive, herbicide compositions, which are suitable for application as a spray, include about 8% to about 100% w/w %, more preferably about 12% to about 30% w/w %, and more preferably from about 15% to about 25% by weight of a herbicidally active limonene component; from about 0.05% to about 10% w/w %, more preferably about 0.1% to about 0.5% w/w %, and more preferably from about 0.2% to about 0.4% by weight of an emulsifying agent; from about 0.02% to about 1.0% w/w %, more preferably about 0.05% to about 0.5% w/w %, and more preferably from about 0.1% to about 0.2% by weight of a wetting agent; and the balance of water or other selected hydrophilic solvent. In one preferred embodiment, there are provided herbicide compositions comprising a herbicidally active limonene component at a concentration of at least about 8% w/w %, an emulsifying agent effective to dissolve or disperse the herbicidally active limonene component in water, in an effective amount, a wetting agent at a concentration of at least about 0.02% w/w % and a hydrophilic solvent, preferably water.

In still another embodiment of the invention, the herbicide composition includes a wetting agent effective to improve the wetting and penetration properties of the composition and has a pH greater than 5. In another embodiment, the herbicide composition, including a wetting agent, has a pH from about 5 to about 10. In yet another embodiment, the pH is from about 6 to about 8, and in yet another embodiment, the pH is from about 8 to about 10. Examples of wetting agents and pH modifiers that can be selected for use in connection with the invention include those described above as non-limiting examples.

Thus, in certain preferred embodiments of the inventive, herbicide compositions, which are suitable for application as a spray, include about 8% to about 100% w/w %, more preferably about 12% to about 30% w/w %, and more preferably from about 15% to about 2 5% by weight of a herbicidally active limonene component; from about 0.05% to about 10% w/w %, more preferably about 0.1% to about 0.5% w/w %, and more preferably from about 0.2% to about 0.4% by weight of an emulsifying agent; from about 0.02% to about 1.0% w/w %, more preferably about 0.05% to about 0.5% w/w %, and more preferably from about 0.1% to about 0.2% by weight of a wetting agent; a pH modifier in an amount effective to maintain a pH greater than 5; and the balance of water or other selected hydrophilic solvent. In one preferred embodiment, there are provided herbicide compositions comprising a herbicidally active limonene component at a concentration of at least about 8% w/w %, an emulsifying agent effective to dissolve or disperse the a herbicidally active limonene component in water, in an effective amount, a wetting agent at a concentration of at least about 0.02% w/w %; a pH modifier effective to maintain a pH greater than 5, and a hydrophilic solvent, preferably water.

The herbicide compositions of this invention can be prepared by entirely conventional procedures known to those of ordinary skill in the art. For example, the compositions can be made by preparing an aqueous mixture of the water, the emulsifying agent and the herbicidally active limonene component. The resulting mixture can then be agitated until a dispersion or emulsion is formed. In one manner of making a herbicide composition according to the invention, each non-aqueous component can be added serially into a container, with stiffing, preferably for at least about 10 minutes after the addition of each component before adding the next component. After all of the non-aqueous components are mixed, the batch is agitated for another 10 minutes and the water can be mixed in to provide the herbicide composition. It can then be tested for quality control, filtered and filled into suitable containers for shipment, storage or immediate use.

The invention has been described thus far in terms of the final herbicide composition, and inventive herbicides can be made, sold and shipped as ready-to-use solutions. It is understood, however, that an excellent manner of providing a herbicide composition to an end user is by first preparing a concentrate formulation that is then diluted with water or other hydrophilic solvent by the end user to provide a herbicide composition for application to target weeds or other vegetation. Thus, herbicide compositions in accordance with the invention can be packaged as ready-to-use herbicides, or can be packaged as herbicide concentrate formulations. Where an inventive herbicide is to be used in a relatively small quantity, such as for home uses, the herbicide can be packaged in a conventional ready-to-use dispensing system. In contrast, when the end user is a farmer or professional applicator who intends to use the herbicide on a large area, it would be more desirable to provide a herbicide concentrate formulation that is ready for dilution. As used herein, the terms "formulation" and "herbicide formulation" are intended to refer to such a concentrate.

In one embodiment, the formulation includes a herbicidally active limonene component mixed with an emulsifying agent. In this embodiment, the formulation, along with a pH modifier, a wetting agent, or both (which can be obtained separately or provided with the formulation in a kit) are mixed with water or other hydrophilic solvent by the end user, for example, in a commercial sprayer. In another embodiment, the pH-buffering agent, the wetting agent, or both, are premixed with the herbicidally active limonene component and the emulsifying agent to provide a formulation that can be mixed directly with water or other hydrophilic solvent to provide a herbicide composition. of course, it is also possible to provide all of the ingredients separately to an end user, with instructions regarding mixing the ingredients together to provide a herbicide composition or a herbicide formulation.

In a particularly preferred embodiment, the herbicide formulation includes a herbicidally active limonene component mixed with an emulsifying agent, and is provided separately from the pH modifier, the wetting agent, or both. A person of ordinary skill in the art will appreciate that the function of the emulsifying agent is to emulsify the herbicidally active limonene component with water, and the amount of emulsifying agent to include in a herbicide formulation or a herbicide composition is related to the amount of limonene in the formulation, irrespective of how diluted the limonene will be in the final herbicide, composition. Thus, whether the herbicide formulation is ultimately mixed with water in a water-to-formulation ratio of, for example, 1:1, 3:1 or higher, the amount of emulsifying agent per unit limonene can remain unchanged. In contrast, the amount of pH modifier that would desirably be included in a herbicide composition can depend upon the volume and the initial pH of water mixed with the formulation; and the amount of wetting agent that would desirably be included in a herbicide composition is dependent upon the total volume of the herbicide composition. Therefore, the emulsifying agent can advantageously be mixed with the herbicidally active limonene component in a herbicide formulation, while the pH modifier and the wetting agent are desirably added at the time the herbicide formulation is mixed with water to provide the final herbicide composition.

In certain preferred embodiments of the invention, there are provided herbicide formulations comprising a herbicidally active limonene component at a concentration of at least about 8% (w/w %), and an emulsifying agent at a concentration of from about 0.5% to about 10% (w/w %). In another embodiment, a herbicide formulation is provided that comprises a herbicidally active limonene component at a concentration of at least about 8% (w/w %), an emulsifying agent at a concentration of from about 0.5 to about 10% (w/w %), and a pH modifier in an amount effective to maintain the pH of the final herbicide composition above 5. In another embodiment, a herbicide formulation is provided that comprises a herbicidally active limonene component at a concentration of at least about 8% (w/w %), an emulsifying agent at a concentration of from about 0.5 to about 10% (w/w %), and a wetting agent at a concentration of from about 0.2% to about 10% (w/w %). In yet another embodiment, a herbicide formulation is provided that comprises a herbicidally active limonene component at a concentration of at least about 8% (w/w %), an emulsifying agent at a concentration of from about 0.5 to about 10% (w/w %), a wetting agent at a concentration of from about 0.2% to about 10 (w/w %); and a pH modifier in an amount effective to maintain the pH of the final herbicide composition above 5.

Said formulations can advantageously be mixed with water, and optionally one or more additional ingredients, at or near the location where the end user intends to apply the herbicide composition to plants. Thus, the invention provides in one aspect a method for making a herbicide composition that includes providing a liquid herbicide formulation, the herbicide formulation including a herbicidally active limonene component and an emulsifying agent; diluting the formulation with water to provide a herbicide composition; and mixing into the herbicide composition a pH modifier effective to provide a pH greater than 5 in the composition. In another aspect, the invention provides a method for making a herbicide composition that includes providing a liquid herbicide formulation, the herbicide formulation including a herbicidally active limonene component and an emulsifying agent; diluting the formulation with water to provide a herbicide composition; and mixing into the herbicide composition a wetting agent. In yet another aspect, there is provided a method for making a herbicide composition that includes providing a liquid herbicide formulation, the herbicide formulation including a herbicidally active limonene component and an emulsifying agent; diluting the formulation with water to provide a herbicide composition; and mixing into the herbicide composition a wetting agent and a pH modifier effective to provide a pH greater than 5. The invention also provides a method for making a herbicide composition that includes providing a liquid herbicide formulation, the herbicide formulation including a herbicidally active limonene component, an emulsifying agent and a pH modifier effective to provide a pH greater than 5 in the formulation; diluting the formulation with water to provide a herbicide composition; and mixing into the herbicide composition a wetting agent.

A herbicidal formulation made or selected in accordance with the present invention can also be packaged or otherwise provided together with additional components in a kit. In one embodiment of the invention, a kit for non-selective burn down of plants is provided that includes a container having therein a liquid herbicide formulation, the herbicide formulation including a herbicidally active limonene component, an emulsifying agent and a pH modifier effective to provide a pH greater than 5; and instructions, recorded in a medium, for diluting the formulation to provide a herbicide composition. In another embodiment, also recorded in the medium are instructions for applying the herbicide composition to a pre-selected area for killing, controlling or suppressing plants growing in the area.

In another embodiment, a kit for non-selective burn down of plants is provided that includes a container having therein a liquid herbicide formulation, the herbicide formulation including a herbicidally active limonene component and an emulsifying agent; and instructions, recorded in a medium, for diluting the formulation with water and adding a pH modifier effective to provide a pH greater than 5. In another embodiment, also recorded in the medium are instructions for applying the herbicide composition to a pre-selected area for indiscriminately killing, controlling or suppressing plants growing in the area.

In another form of the invention, there is provided a kit for non-selective burn down of plants that includes a container having_ therein a liquid herbicide, the herbicide including water, a herbicidally active limonene component, an emulsifying agent and a wetting agent; and instructions for applying the herbicide to a pre-selected area for killing, controlling or suppressing weeds or other plants in the area.

Also provided by the invention is a kit for nonselective burn down of plants that includes a container having therein a liquid herbicide formulation, the herbicide formulation including a herbicidally active limonene component and an emulsifying agent; and instructions, recorded in a medium, for diluting the formulation and mixing in a wetting agent to provide a herbicide composition. In another embodiment, also recorded in the medium are instructions for applying the herbicide composition to a pre-selected area for killing, controlling or suppressing plants growing in the area.

In another form of the invention, a kit for nonselective burn down of plants is provided that includes a container having therein a liquid herbicide, the herbicide including water, a herbicidally active limonene component, an emulsifying agent, a wetting agent and a pH modifier effective to provide a pH greater than 5; and instructions for applying the herbicide to a pre-selected area for indiscriminately killing plants growing in the area. Another kit for non-selective burn down of plants is provided that includes a container having therein a liquid herbicide formulation, the herbicide formulation including a herbicidally active limonene component, an emulsifying agent and a pH modifier effective to provide a pH greater than 5; and instructions, recorded in a medium, for diluting the formulation and adding a wetting agent to provide a herbicide composition. Still another embodiment of the invention is a kit for non-selective burn down of plants that includes a container having therein a liquid herbicide formulation, the herbicide formulation including a herbicidally active limonene component and an emulsifying agent; and instructions, recorded in a medium, for diluting the formulation with water and adding a wetting agent and a pH modifier effective to provide a pH greater than 5.

In addition to inclusion of herbicide formulations in a kit, as described above, the invention also contemplates providing a pre-made, complete herbicide composition with other components in a kit. Thus, in another, form of the invention, a kit for non-selective burn down of plants is provided that includes a container having therein a liquid herbicide, the herbicide including water, a herbicidally active limonene component, an emulsifying agent and one or more member selected from a wetting agent and a pH modifier effective to provide a pH greater than 5; and instructions, recorded in a medium, for applying the herbicide to a pre-selected area for indiscriminately killing plants growing in the area.

An inventive herbicide composition or herbicide concentrate formulation in accordance with the invention can be prepared to include a variety of other beneficial ingredients in addition to the ingredients discussed above. By "beneficial", it is meant that the additional ingredient provides some additional functionality, efficacy, quality or other desirable attribute the herbicide or herbicide concentrate. For example, the herbicidally active limonene component may be blended with other, cheaper, and somewhat less volatile oils to form effective herbicides. Various natural oils (such as cottonseed oil, soybean oil, rapeseed oil, sunflower oil, safflower oil, olive oil, coconut oil, coconut milk, corn oil, grape seed oil and peanut oil) have been reported by others to lack significant herbicidal activity; however, they can be blended with the herbicidally active limonene component of the present invention to form effective herbicidal compositions.

One or more other ingredients may optionally be included in the compositions of the invention in order to provide aesthetic or other beneficial properties thereto. Such optional ingredients are, for example, antimicrobial agents, preservatives, deodorizers, coloring agents, fragrances, additional emulsifiers, additional solubilizers, corrosion inhibitors and additional solvents. The only requirement is that for any particular composition such optional ingredients be compatible with the other ingredients present in the composition or formulation.

By way of example, optional ingredients that can be incorporated include the following: an antimicrobial, such as, for example, phenolic compounds such as o-phenylphenol and o-benzyl[p-chlorophenol]; quaternary ammonium compounds such as alkyl dimethyl benzyl ammonium chloride, octyl decyl dimethyl ammonium chloride, dioctyl dimethyl ammonium chloride, didecyl dimethyl ammonium chloride and alkyl dimethyl benzyl ammonium saccharinate; a deodorizer, such as, for example, N-alkyl-N-ethylmorpholinium ethyl sulfate; and a corrosion inhibitor, such as, for example, mono- and triethanolamine, ammonium hydroxide, sodium molybdate, sodium benzoate and tetra sodium ethylenediamine tetraacetate.

Other optional ingredients, as well as the amounts of the optional ingredients that can be employed, can readily be determined by one skilled in the art. For example, the phenolic and quaternary ammonium antimicrobial agents generally will not exceed a concentration of about 0.2 percent by weight in the final herbicide composition.

In order to provide a reasonable shelf-life to the herbicide compositions, it is preferable that a preservative be added to the composition. One such suitable preservative is sodium benzoate commercially supplied by Pfizer, Inc. Other commercially available preservatives used for preserving food, as would be known to those of ordinary skill in the art, may also be suitably used.

The beneficial agents described above, and many others, as would be contemplated by a person of ordinary skill in the art, are well known to those skilled in the art and are available commercially.

In a further aspect, the invention provides a method for killing, controlling or suppressing unwanted plant growth, wherein a herbicide composition provided in accordance with the present invention is applied to the unwanted plant or plants. The composition is then permitted to remain in contact with the plant, preferably the leaves of the plant, for a period of time sufficient to kill, control or suppress the plant. The time required for effective treatment of a given plant is dependent upon a variety of factors including, but not limited to concentration, spray coverage, pH of the herbicide solution, the species of the plant, the size/age/maturity of the plant, the availability of leaf surfaces or other green surfaces, and ambient conditions.

In an agricultural setting, spray applications with standard equipment typically use 20 to 35 gallons per acre for good coverage. Commercial electrostatic sprayers can bring the rates down significantly to less than 10 gal/acre and still achieve good coverage. In one manner of practicing the invention, the method includes spraying the herbicide on the area at a rate of from about 5 gal/acre to about 40 gal/acre. In another preferred manner of practicing the invention, the method includes spraying the herbicide on the area at a rate of from about 5 gal/acre to about 35 gal/acre.

In a homeowner or professional landscaping setting, spray applications on weeds are typically susceptible to runoff. Depending concentration of the herbicidally active limonene component in the herbicide composition as well as the density and maturity/size of the weeds, the equivalent spray volume per acre could be from a couple of quarts to 100 gallons per acre or more.

The invention will be further described with reference to the following specific Examples. It will be understood that these Examples are intended to be illustrative and not restrictive in nature.

EXAMPLE 1

Preparation of Herbicide Formulation

A herbicide formulation (MM-01) was prepared in accordance with the invention to include 94.0 w/w % limonene with the following emulsifiers: 1.3 w/w % Tergitol™ NP-8 (nonylphenol ethoxylate surfactant), 2.0 w/w % Tergitol™ NP-9 (nonoxynol 9.5 surfactant) and 2.7 w/w % Pluracol® P-425 (polypropylene glycol surfactant). The resulting formulation contains 88% limonene w/w %. For making a 100 gallon batch of this herbicide formulation, each component is added one by one and the mixture is stirred for 10 minutes after each addition and before adding the next component, to ensure complete and homogeneous blending of the components. After all the components are mixed, the batch is agitated for another 10 minutes, tested for quality control, filtered and filled into suitable containers.

Preparation of Herbicide Compositions

The formulation was diluted with water to a 3:1 ratio by volume, represented as water:herbicide formulation ratio, to provide a herbicide composition (22% limonene w/w %). It is estimated that the pH of the 3:1 ratio composition was 4.5. The pH was lowered to 4 with lemon juice in a first test batch and raised to pH 9 with potassium carbonate in a second test batch. In addition, a herbicide composition with the 3:1 ratio was modified by adding 0.05% silicone based surfactant (Silwet) in a third test batch.

Protocol for Testing Herbicide Compositions

This field trial was conducted in Northern California during November, 2004. Each of the herbicide compositions described above was sprayed onto postemergent plants with backpack spray equipment to ensure good coverage without runoff. Primary weeds evaluated were Bermuda grass, fescue, and strawberry clover.

Color and wilting ratings were taken at 2 hours, 1 day, 2 days, and 7 days after treatment. Data collected for the test compositions were compared to an untreated control (UTC) and an area of vegetation treated with Paraquat (Gramoxone®). This trial contained 3 reps per treatment (except the paraquat treatment which was a single strip). Treatments were randomly distributed within a rep.

Color and wilting ratings were taken at 2 hours, 1 day, 2 days and 7 days after treatment. Results are set forth in FIGS. 1-6.

Discussion

In this trial, in which all treatment received 3:1 ratios (water:limonene formulation), the plants responded very rapidly. In broadleaf plants, discoloration followed by necrosis, and blackening of the leaf tissue occurred within 2 to 4 hours. In grasses, the response was more gradual, and leaves tended to gradually change from green to yellow to brown.

All MM-01 treatments resulted in a visual, burn down response within 2 hours. After Day 1, all MM-01 treatments were significantly different (P<0.05) from the untreated control (UTC).

The best MM-01 treatments were with 0.05% silicone surfactant and at pH 9. At days 2 and 7, both were significantly better than the other treatments. At days 2 and 7, the surfactant and pH 9 treatments were numerically equivalent to the paraquat standard.

Wilting responses increased over time for all MM01 treatments. Color ratings for MM-01 did not change significantly over time.

The differences attributed to pH and surfactant are very apparent. In the 7 days after treatment, the impact of surfactant on wilting and color was tallied and the results are set forth in Table I below:

TABLE I

| Effect Measured | MM01 3:1 ratio (ph 4.5) | MM01 (3:1 ratio) + 0.05% | Difference | Difference |
|---|---|---|---|---|
| Wilting | 7 | 3.33 | 0.66 | 24.7% |
| Color | 3.67 | 5.00 | 1.33 | 36.2% |
| Average differences | | | 1.00 | 30.5% |

At 7 days after treatment, the impact of pH on wilting and color was also tallied, and the results are set forth in Table II below:

TABLE II

| Effect Measured | pH 4 | pH 9 | Difference | Difference |
|---|---|---|---|---|
| Wilting | 3.00 | 3.67 | 0.67 | 22.3% |
| Color | 3.33 | 4.67 | 1.34 | 40.2% |
| Average differences | | | 1.01 | 31.3% |

The use of a nonionic, silicon surfactant increased the wilting ratings by 24.7% and color by 36.2%.

The use of pH 9-increased the wilting ratings by 22.3% and color by 40.2%.

EXAMPLE 2

Figure 7:
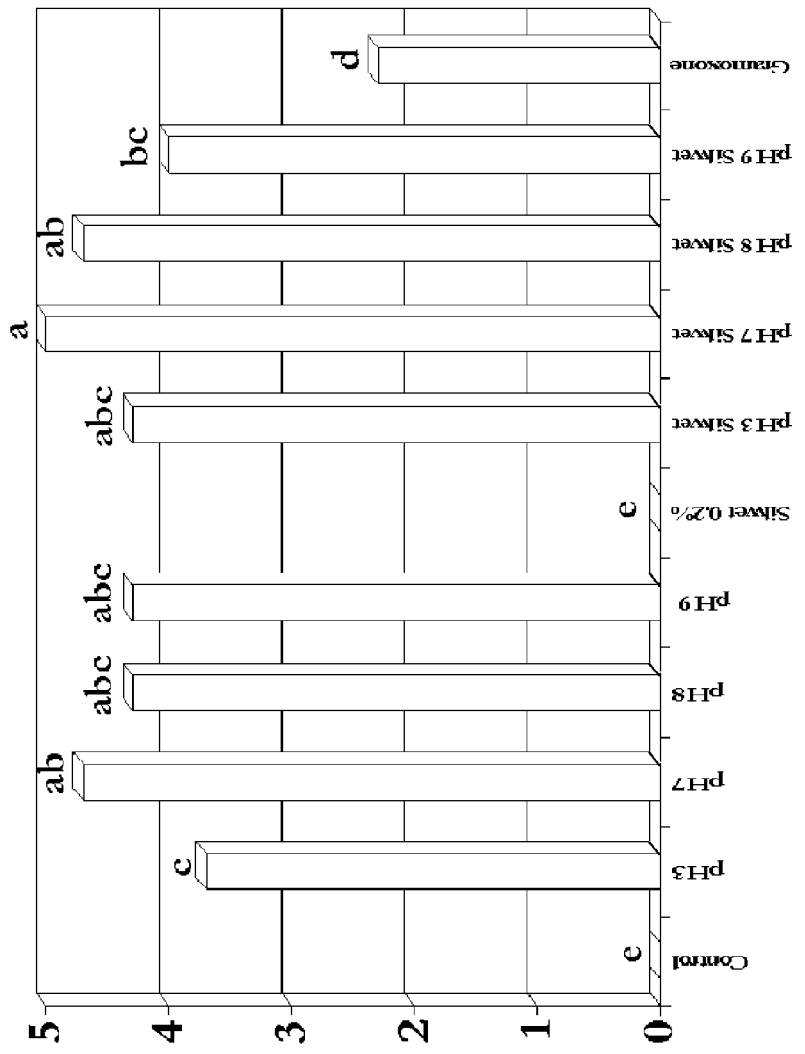
FIG. 7 is a bar graph setting forth results from a field study on lambsquarters conducted in Florida in January of 2005. Ratings are based on 0 to 10 (no damage to dead). Statistical analysis is by Duncan's MRT ($P<0.05$). Treatments with the same letter or letter combination are not significantly different.

A field trial was conducted in Zellwood, Fla. The same formulation described in Example 1 was used in the Florida trial. All limonene treatments were made at a 3:1 ratio by volume, represented as water:herbicide formulation ratio, to provide a herbicide composition of 22% limonene (w/w %). Four reps per treatment were used; all treatments were randomly distributed within a rep. The weed species was common lambsquarters (1 to 2 feet in height). Treatments applied were pH 3, 7, 8 and 9 with and without a silicone surfactant, Silwet; each treatment was sprayed until runoff. The commercial burn down standard, Gramoxone (paraquat) was included. Readings were taken at 1 and 2 hours, and 1, 3 and 7 days. An immediate wilting of the lambsquarters was observed with all limonene treatments starting at 1 hour. Effects with Gramoxone (paraquat) were first observed on day 1 and improved by Day 3. After the first 2 hours limonene effects were stabilized. Results after 3 days are set forth in FIG. 7.

Large common lambsquarters are a difficult to control weed for limonene, making it a good candidate to evaluate difference caused by pH and surfactants. Evaluating the effect of pH, pH 7 gave the best response with and without surfactant. Without surfactant, it was significantly better than pH 3.

Side by side comparisons with the surfactant can also be made. Although not statistically significant, surfactant increased limonene activity with almost every pH with an average increase of 6.1% (see Table)

TABLE III

| Treatment | pH | pH + Silwet | Difference | % Difference |
|---|---|---|---|---|
| pH 3 | 3.7 | 4.3 | 0.6 | 16.2% |
| pH 7 | 4.7 | 5.0 | 0.3 | 6.4% |
| pH 8 | 4.3 | 4.7 | 0.4 | 9.3% |
| pH 9 | 4.3 | 4.0 | −0.3 | −7.5% |
| Average differences | | | 0.25 | 6.1 |

EXAMPLE 3

A series of trials were conducted at Michigan State University (MSU) in East Lansing, Mich. to optimize the response with limonene on key weeds. Grasses responded strongly to limonene, which diminishes their suitability for pH and surfactant evaluations since all treatments gave an excellent herbicidal response. Mature common lambsquarters does not respond well to limonene making it a good candidate for these trials.

The same formulation described in Example 1 was used in the MSU greenhouse trials. Four reps per treatment were used. All limonene treatments were made at a 3:1 ratio by volume, represented as water:herbicide formulation ratio, to provide a herbicide composition of 22% limonene (w/w %). The herbicide composition was applied in spray chamber designed to mimic an agricultural application. Spray volume was 60 gallons per acre and the spray nozzle pressure was 40 psi. The weed species was common lambsquarters (1 to 2 feet in height). Treatments applied were pH 3, 5, 7, 8 and 9 without any surfactant. A single reading was taken at day 4. Results are set forth in FIG. 8.

There was a strong trend towards a pH response with pH 5 being the optimal pH. pH 7 and 8 had numerically better responses than pH 3 (11.4% and 7.5% respectively) or unadjusted limonene at pH 4.2 (14.7% and 10.6% respectively). pH 9 was significantly lower than the other treatments.

All surfactants improved the performance of the limonene formulation in water. The silicon based product, Sylgard, was significantly better by comparison.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A herbicidal composition effective against mature weeds, comprising: water, about 8% to about 30% by weight of a herbicidally active limonene component, 0.05% to 10% by weight of a polyethoxylated castor oil emulsifying agent, and 0.05% to 10% by weight of an alcohol ethoxylate surfactant, wherein said composition has a pH greater than 5.

2. A composition according to claim 1 wherein the composition has a pH of from about 6 to about 8.

3. A composition according to claim 1 wherein said composition comprises 15% to 25% by weight of a herbicidally active limonene component.

4. A composition according to claim 1 wherein said composition further comprises from about 0.02% to about 1.0% by weight of a wetting agent.

5. A composition according to claim 4 wherein the wetting agent is a silicone surfactant.

6. A composition according to claim 5 wherein the wetting agent is selected from the group consisting of anionic and nonionic surfactants and a mixture of any one or more thereof.

7. A composition according to claim 1 wherein the composition includes a pH modifier selected from the group consisting of potassium carbonate, potassium hydroxide and sodium hydroxide.

8. A method for killing, controlling or suppressing a plant, comprising:
   a) providing a liquid herbicidal composition according to claim 1, and
   b) spraying the herbicidal composition onto one or more leaves of the plant.

9. The method according to claim 8 wherein said spraying comprises spraying in a manner whereby the herbicidal composition contacts at least or about 60% of the surface area of the plant's leaf or leaves.

10. The method according to claim 8 wherein the composition has a pH of from about 6 to about 8.

11. The method according to claim 8 wherein the pH modifier is selected from the group consisting of potassium carbonate, potassium hydroxide and sodium hydroxide.

12. The method according to claim 8 wherein the herbicidal composition further includes a wetting agent.

13. The method according to claim 12 wherein the wetting agent is a silicone surfactant.

14. The method according to claim 12 wherein the wetting agent is present in the composition at a concentration of from about 0.02% to about 1%.

15. The method according to claim 12 wherein the wetting agent is selected from the group consisting of anionic and nonionic surfactants and a mixture of any one or more thereof.

16. The method of claim 8 wherein said spraying comprises spraying the herbicide on the area at a rate of from about 0.5 gal/acre to about 100 gal/acre.

* * * * *